United States Patent [19]

Sundeen et al.

[11] 4,122,083
[45] Oct. 24, 1978

[54] 1,2,3,4-TETRAHYDROPYRIDO[4',3':4,5]-THIAZOLO-[3,2-a]BENZIMIDAZOLES

[75] Inventors: Joseph E. Sundeen, Yardley, Pa.; Tamara Dejneka, Skillman, N.J.

[73] Assignee: E. R. Squibb & Sons, Inc., Princeton, N.J.

[21] Appl. No.: 869,737

[22] Filed: Jan. 16, 1978

[51] Int. Cl.$^2$ ............................................. C07D 513/14
[52] U.S. Cl. .................. 260/294.8 A; 260/293.89; 260/294.8 C
[58] Field of Search ................. 260/294.8 A, 293.55

[56] References Cited
PUBLICATIONS
Arya, V., et al., Indian J. Chem., 11, 744 (1973).
Arya, V., et al., Indian J. Chem., 14B, 759 (1976).

Chemical Abstracts, 71, 22067v (1969) [Krasovskii, A., et al., Khim. Geterotsikl, Soedin, 1969, (2), 321-324].

Primary Examiner—Henry R. Jiles
Assistant Examiner—Richard A. Schwartz
Attorney, Agent, or Firm—Lawrence S. Levinson; Merle J. Smith

[57] ABSTRACT

The new compounds 1,2,3,4-tetrahydropyrido[4',3':4,5]-thiazolo[3,2-a]benzimidazole and derivatives thereof which have the general formula

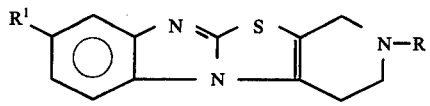

are useful as anti-inflammatory agents.

10 Claims, No Drawings

1,2,3,4-TETRAHYDROPYRIDO[4′,3′:4.5]-THIAZOLO-[3,2-a]BENZIMIDAZOLES

SUMMARY OF THE INVENTION

This invention relates to 1,2,3,4-tetrahydropyrido[4′,3′:4,5]thiazolo[3,2-a]benzimidazole and derivatives thereof which have the general formula

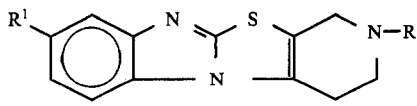 (I)

and salts thereof.

R represents hydrogen, lower alkanoyl, unsubstituted or substituted lower alkyl (wherein the substituted lower alkyl bears one or two cyano, hydroxy, carbolower alkoxy, or trifluoromethyl groups); lower alkenyl or lower alkynyl; or unsubstituted or substituted phenyl-lower alkyl (wherein the substituted phenyl-lower alkyl bears one or two halogen, lower alkyl, lower alkoxy or nitro groups on the phenyl ring).

$R^1$ represents hydrogen, halo, nitro or lower alkoxy.

DETAILED DESCRIPTION OF THE INVENTION

The lower alkyl groups represented by the symbols in formula I are straight or branched chain aliphatic hydrocarbon radicals having up to seven carbon atoms. Methyl, ethyl, propyl, isopropyl, butyl, isobutyl, t-butyl, pentyl, hexyl, and heptyl are illustrative. The $C_1$–$C_4$ members, and especially the $C_1$–$C_2$ members, are preferred. The lower alkenyl and lower alkynyl groups are monounsaturated groups of the same type having a double or triple bond, respectively. The $C_2$–$C_4$ members are preferred, especially allyl and propargyl.

The lower alkoxy groups are radicals having up to seven carbon atoms of the same type. Illustrative are methoxy, ethoxy, propoxy, isopropoxy, butoxy and the like. The $C_1$–$C_4$ and $C_1$–$C_2$ members are similarly preferred.

The lower alkanoyl groups are the acyl radicals of the lower fatty acids (up to seven carbons), e.g., acetyl, which is especially preferred, propanoyl, isopropanoyl, butanoyl, pentanoyl, etc. Those members having up to 4 carbons are also preferred.

The four common halogens are contemplated by the term "halo," chlorine and bromine, especially the first, being preferred.

The substituted lower alkyl groups and substituted phenyl-lower alkyl groups are those bearing one or two (preferably one) substituent groups (as enumerated above) on the alkyl radical or phenyl radical, respectively. (The preferences referred to above apply to the alkyl group in the phenyl-lower alkyl radical.) Illustrative are cyanoethyl, carboethoxyethyl, carboethoxymethyl, 2-hydroxyethyl, 3-hydroxypropyl, 3,4-dimethoxyphenethyl, 4-bromophenylmethyl, 4-nitrophenylmethyl, 4-methoxyphenylmethyl.

Products wherein only one or R and $R^1$ is other than hydrogen and the substituent is unsubstituted constitute a preferred class.

Preferred are those compounds of formula I wherein R is hydrogen, lower alkanoyl or phenyl-alkyl, especially hydrogen, acetyl or benzyl; and $R^1$ is hydrogen or methoxy, especially hydrogen. The examples include especially preferred single embodiments.

The compounds of formula I are produced by a series of reactions beginning with an acyl piperidone of the formula

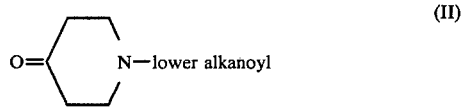 (II)

e.g., N-acetyl-4-piperidone, which is converted with bromine, e.g., in glacial acetic acid at a reduced temperature of about 10° C. to a compound of the formula

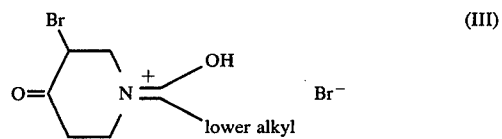 (III)

When the compound of formula III is made to react with a 2-mercaptobenzimidazole of the formula

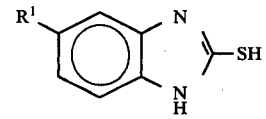

e.g., in an inert organic solvent such as an alcohol like ethanol, methanol, propanol or butanol, at an elevated temperature within the range of about 50° to 100° C., there results a compound of the formula

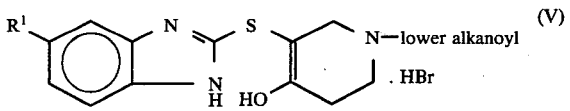 (V)

Additional heating at a temperature within the range of about 160° to 170° C. for a period of about ½ hour then yields a product of the formula

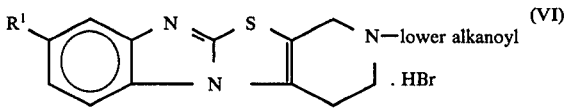 (VI)

This is a product of formula I wherein R is lower alkanoyl (in the salt form). Neutralization, e.g., with an alkali metal compound like sodium bicarbonate, yields the free product of formula I.

When the product of formula I is hydrolyzed, e.g., with a strong base such as an alkali metal hydroxide like sodium hydroxide, potassium hydroxide or the like, at an elevated temperature in the range of about 70° to 100° C., a product of formula I wherein R is hydrogen is obtained.

This product can then be used to obtain products of formula I wherein R is lower alkyl, phenyl-lower alkyl, lower alkenyl, lower alkynyl, or members wherein the first two groups are substituted, by alkylating the product wherein R is hydrogen, e.g., with a lower alkyl halide, lower alkenyl halide, lower alkynyl halide or phenyl-lower alkyl halide (or substituted analogs thereof) like methyl iodide, propyl bromide, allyl bromide, propargyl bromide, benzyl bromide, phenethyl bromide, ethyl bromoacetate, etc., in an inert hydrocarbon solvent like toluene, benzene, xylene or the like, in the presence of an organic base acid acceptor such as trialkylamine like triethylamine, ethyl diisopropylamine or the like at an elevated temperature in the range of about 80° to 140° C. or by heating that starting material with a lower alkenylnitrile like acrylonitrile or ester like ethyl acrylate in a hydrocarbon solvent like those named above at an elevated temperature in the range of about 80° to 100° C.

The compounds of formula I form salts which are also part of this invention. The salts include acid-addition salts, particularly the non-toxic physiologically acceptable members. The bases of formula I form salts by reaction with one or more equivalents of a variety of common inorganic and organic acids providing well known acid addition salts such as hydrohalides (especially hydrochloride and hydrobromide), sulfate, nitrate, borate, phsophate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating and purifying the product or to obtain another salt, e.g., by forming and precipitating a readily obtainable salt in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid.

The new compounds of this invention have anti-inflammatory properties and are useful as anti-inflammatory agents, for example, to reduce local inflammatory conditions such as those of an edematous nature of resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the Mouse Active Arthus assay. The active substance can be utilized in compositions such as tablets, capsules, solutions or suspensions containing up to about 500 mg. per unit of dosage of a compound or mixture of compounds of formula I or physiologically acceptable acid addition salt thereof. They may be compounded in conventional manner with a physiologically acceptable vehicle or carrier, excipient, binder, preservative, stabilizer, flavor etc. as called for by accepted pharmaceutical practice.

The following examples are illustrative of the invention and provide representative process details. Other members can be prepared in the same manner by substitution of the appropriate starting material. All temperatures are in degrees Celsius.

EXAMPLE 1

2-Acetyl-1,2,3,4-tetrahydropyrido[4',3':4,5]-thiazolo[3,2-a]benzimidazole (a) N-Acetyl-4-piperidone (14.1 g., 0.1 mole) is dissolved in 50 ml. of glacial acetic acid. This solution is cooled to 10° and bromine (5.0 g., 0.1 mole) in 20 ml. of glacial acetic acid is added dropwise. After the addition, the reaction mixture is stirred at ambient temperature until complete decolorization of the bromine occurs and a white crystalline solid precipitates out. The solid is filtered, washed with ether and dried in vacuo to yield 28.0 g. of product, N-acetyl-3-bromo-4-piperidone, hydrobromide, m.p. 160°–172° (dec.).

(b) 2-Mercaptobenzimidazole (3.0 g., 0.02 mole) is suspended in 30 ml. of absolute ethanol. This solution is heated to 60° and the product of part a (6.2 g., 0.02 mole) is added in small portions. Reaction is vigorous and heating is continued until all the alpha-bromoketone has been added. The reaction mixture is stirred at 40° for one hour. Ethanol is distilled off at atmospheric pressure and heating is continued and maintained at 160°/170° for 20 minutes. The pot residue is cooled, dissolved in water and neutralized with aqueous sodium bicarbonate. The product is extracted with chloroform. The chloroform extract is dried with sodium sulfate, filtered and concentrated in vacuo to yield 4.0 g. of 2-acetyl-1,2,3,4-tetrahydropyrido[4',3':4,5]-thiazolo[3,2-a]benzimidazole which is recrystallized from ethanol to yield 1.8 g., m.p. 181°–186°.

EXAMPLE 2

1,2,3,4-Tetrahydropyrido[4',3':4,5]thiazolo[3,2-a]benzimidazole

2-Acetyl-1,2,3,4-tetrahydropyrido[4',3':4,5]-thiazolo[3,2-a]benzimidazole (13.5 g., 0.05 mole) is dissolved in 100 ml. of absolute ethanol. Sodium hydroxide (3 ml. of 50% aqueous sodium hydroxide) is added and the reaction mixture is digested on the steam cone for one hour. It is then concentrated in vacuo and the residue is washed with water. The white crystalline material is filtered and dried to yield 7.3 g. of 1,2,3,4-tetrahydropyrido[4',3':4,5]thiazolo[3,2-a]benzimidazole, which is recrystallized from methanol-chloroform to yield 4.3 g. of analytical sample, m.p. 238°–243°.

EXAMPLE 3

1,2,3,4-Tetrahydro-2-(phenylmethyl)pyrido[4',3':4,5]-thiazolo[3,2-a]benzimidazole 1,2,3,4-tetrahydropyrido[4',3':4,5]thiazolo[3,2-a]benzimidazole (1.9 g., 0.008 mole) is dissolved in 100 ml. of boiling toluene. Triethylamine (5 ml.) is added at 80°. Benzyl bromide (1.7 g., 0.01 mole) is dissolved in 5 ml. of toluene and added dropwise to the reaction mixture. After the addition, the reaction mixture is refluxed for two hours. It is filtered and concentrated in vacuo to yield 3.6 g. of oil. Ethyl acetate is added and the product, 1,2,3,4-tetrahydro-2-(phenylmethyl)-pyrido[4',3':4,5]thiazolo[3,2-a]benzimidazole crystallizes. This is filtered and recrystallized from ethyl acetate:ethanol (10:1) to yield 1.4 g. of analytical product, m.p. 124°–129°.

EXAMPLE 4

2-Propyl-1,2,3,4-tetrahydropyrido[4',3':4,5]-thiazolo[3,2-a]benzimidazole

By substituting an equivalent amount of propyl bromide for the benzyl bromide in the procedure of Example 3, 2-propyl-1,2,3,4-tetrahydropyrido[4',3':4,5]-thiazolo[3,2-a]benzimidazole is obtained.

EXAMPLE 5

2-Carboethoxymethyl-1,2,3,4-tetrahydropyrido[4',3':4,5]thiazolo-[3,2-a]benzimidazole By substituting an equivalent amount of ethylbromoacetate for the benzyl bromide in the procedure of Example 3, 2-carboethoxymethyl-1,2,3,4-tetrahydropyrido[4',3':4,5]thiazolo[3,2-a]benzimidazole is obtained.

EXAMPLE 6

2-Allyl-1,2,3,4-tetrahydropyrido[4',3':4,5]thiazolo[3,2-a]benzimidazole

By substituting an equivalent amount of allyl bromide for the benzyl bromide in the procedure of Example 3, 2-allyl-1,2,3,4-tetrahydropyrido[4',3':4,5]thiazolo[3,2-a]benzimidazole is obtained.

EXAMPLE 7

2-Propargyl-1,2,3,4-tetrahydropyrido[4',3':4,5]-thiazolo[3,2-a]benzimidazole

By substituting an equivalent amount of propargyl bromide for the benzyl bromide in the procedure of Example 3, 2-propargyl-1,2,3,4-tetrahydropyrido[4',3':4,5]thiazolo3,2-a]benzimidazole is obtained.

EXAMPLE 8

2-Phenylethyl-1,2,3,4-tetrahydropyrido[4',3':4,5]-thiazolo[3,2-a]benzimidazole

By substituting an equivalent amount of phenethyl bromide for the benzyl bromide in the procedure of Example 3, 2-phenylethyl-1,2,3,4-tetrahydropyrido[4',3':4,5]thiazolo[3,2-a]benzimidazole is obtained.

EXAMPLE 9

2-[(4-Methoxyphenyl)methyl]-1,2,3,4-tetrahydropyrido[4',3':4,5]thiazolo[3,2-a]benzimidazole By substituting an equivalent amount of 4-methoxybenzyl bromide for the benzyl bromide in the procedure of Example 3, 2-[(4-methoxyphenyl)methyl]-1,2,3,4-tetrahydropyrido[4',3':4,5]thiazolo[3,2-a]benzimidazole is obtained.

EXAMPLE 10

2-Butyryl-1,2,3,4-tetrahydropyrido[4',3':4,5]-thiazolo[3,2-a]benzimidazole 1,2,3,4-Tetrahydropyrido[4',3':4,5]thiazolo[3,2-a]benzimidazole (2.29 g., 0.01 mole) in 100 ml. of pyridine at 0° is treated with 1.06 g. (0.01 mole) butyryl chloride. After 24 hours at 5°, the mixture is stripped to a slurry, shaken with sodium bicarbonate and chloroform. Drying and evaporation of the organic solvents gives a solid which is recrystallized from methanol to give pure 2-butyryl-1,2,3,4-tetrahydropyrido[4',3':4,5]-thiazolo[3,2-a]benzimidazole.

EXAMPLE 11

2-(3-Hydroxypropyl)-1,2,3,4-tetrahydropyrido[4',3':4,5]thiazolo[3,2-a]benzimidazole By substituting an equivalent amount of 3-bromo-1-propanol for the benzyl bromide in the procedure of Example 3, 2-(3-hydroxypropyl)-1,2,3,4-tetrahydropyrido[4',3':4,5]thiazolo[3,2-a]benzimidazole is obtained.

EXAMPLE 12

2-(2,2,2-Trifluoroethyl)-1,2,3,4-tetrahydropyrido[4',3':4,5]thiazolo[3,2-a]benzimidazole By substituting an equivalent amount of 2,2,2-trifluoroethyl chloride for the benzyl bromide in the procedure of Example 3, 2-(2,2,2-trifluoroethyl)-1,2,3,4-tetrahydropyrido[4',3':4,5]thiazolo[3,2-a]benzimidazole is obtained.

EXAMPLES 13–24

By substituting an equivalent amount of 2-mercapto-5-nitrobenzimidazole for the 2-mercaptobenzimidazole in the procedure of Example 1b, and then following the procedures of Examples 2 and 3, the following products, respectively, are obtained:

(13)  2-Acetyl-1,2,3,4-tetrahydropyrido[4',3':4,5]-thiazolo[3,2-a]-8-nitrobenzimidazole

(14)  1,2,3,4-Tetrahydropyrido[4',3':4,5thiazolo[3,2-a]-8-nitrobenzimidazole

(15)  2-Phenylmethyl-1,2,3,4-tetrahydropyrido[4',3':4,5thiazolo[3,2-a]-8-nitrobenzimidazole Similarly, by substituting an equivalent amount of 5-chloro-2-mercaptobenzimidazole, 5-bromo-2-mercaptobenzimidazole or 2-mercapto-5-methoxybenzimidazole, respectively, for the 2-mercaptobenzimidazole in the procedure of Example 1b, and then following the procedures of Examples 2 and 3, the following products, respectively, are obtained:

(16)  2-Acetyl-1,2,3,4-tetrahydropyrido[4',3':4,5]-thiazolo[3,2-a]-8-chlorobenzimidazole

(17)  1,2,3,4-Tetrahydropyrido[4',3':4,5]thiazolo[3,2-a]-8-chlorobenzimidazole

(18)  2-Phenylmethyl-1,2,3,4-tetrahydropyrido[4',3':4,5]thiazolo[3,2-a]-8-chlorobenzimidazole

(19)  2-Acetyl-1,2,3,4-tetrahydropyrido[4',3':4,5]-thiazolo[3,2-a]-8-bromobenzimidazole

(20)  1,2,3,4-Tetrahydropyrido[4',3':4,5]thiazolo[3,2-a]-8-bromobenzimidazole

(21)  2-Phenylmethyl-1,2,3,4-tetrahydropyrido[4',3':4,5]thiazolo[3,2-a]-8-bromobenzimidazole

(22)  2-Acetyl-1,2,3,4-tetrahydropyrido[4',3':4,5]-thiazolo[3,2-a]-8-methoxybenzimidazole

(23)  1,2,3,4-Tetrahydropyrido[4',3':4,5]thiazolo[3,2-a]-8-methoxybenzimidazole

(24)  2-Phenylmethyl-1,2,3,4-tetrahydropyrido[4',3':4,5]thiazolo[3,2-a]-8-methoxybenzimidazole

EXAMPLE 25

2-[2-Cyanoethyl]-1,2,3,4-tetrahydropyrido[4',3':4,5]-thiazolo[3,2-]benzimidazole hydrochloride 1,2,3,4-tetrahydropyrido[4',3':4,5]thiazolo[3,2-a]benzimidazole (2.29 g., 0.01 mole) is heated in 100 ml. of toluene at 90° while acrylonitrile (1.06 g., 0.07 moles) is added. After 1 hour at 90°, the mixture is evaporated in vacuo. The residual, crude 2-[2-cyanoethyl]-1,2,3,4-tetrahydropyrido[4',3':4,5]thiazolo[3,2-a]benzimidazole is taken up in isopropanol and treated with excess HCl in isopropanol. This is precipitated by the addition of ether. Recrystallization from isopropanol-ether gives the product, 2-[2-cyanoethyl]-1,2,3,4-tetrahydropyrido[4',3':4,5]thiazolo[3,2-a]benzimidazole hydrochloride.

EXAMPLE 26

2-(2-Carboethoxyethyl)-1,2,3,4-tetrahydropyrido[4',3':4,5]thiazolo[3,2-a]benzimidazole hydrochloride By substituting an equivalent amount of ethyl acrylate in the procedure of Example 25, 2-(2-carboethoxyethyl)-1,2,3,4-tetrahydropyrido[4',3':4,5]thiazolo[3,2-a]benzimidazole and its hydrochloride are obtained.

What is claimed is:

1. A compound of the formula

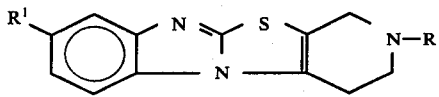

wherein

R is hydrogen, lower alkanoyl, lower alkyl, lower alkenyl, lower alkynyl, phenyl-lower alkyl, substituted lower alkyl bearing cyano, hydroxy, carbolower alkoxy or trifluoromethyl, or substituted phenyl-lower alkyl bearing halogen, lower alkyl, lower alkoxy or nitro;

$R^1$ is hydrogen, halo, nitro or lower alkoxy;
and acid addition salts thereof.

2. A compound as in claim 1 wherein $R^1$ is hydrogen.
3. A compound as in claim 1 wherein R is hydrogen.
4. A compound as in claim 1 wherein R is lower alkyl.
5. A compound as in claim 1 wherein R is lower alkanoyl.
6. A compound as in claim 1 wherein R is phenyl-lower alkyl.
7. A compound as in claim 1 wherein R is hydrogen, lower alkanoyl or phenyl-lower alkyl; and $R^1$ is hydrogen or lower alkoxy.
8. A compound as in claim 2 wherein R is hydrogen.
9. A compound as in claim 2 wherein R is acetyl.
10. A compound as in claim 2 wherein R is phenylmethyl.

* * * * *